(12) United States Patent
Huang

(10) Patent No.: US 7,241,800 B2
(45) Date of Patent: Jul. 10, 2007

(54) ANHYDROUS AMORPHOUS FORM OF FLUVASTATIN SODIUM

(75) Inventor: Le Huang, Nanchang (CN)

(73) Assignee: Mai De Ltd., Northborough, MA (US)

( * ) Notice: Subject to any disclaimer, the term of this patent is extended or adjusted under 35 U.S.C. 154(b) by 391 days.

(21) Appl. No.: 10/802,585

(22) Filed: Mar. 17, 2004

(65) Prior Publication Data

US 2005/0209259 A1    Sep. 22, 2005

(51) Int. Cl.
*C07D 209/12*    (2006.01)
*A61K 31/404*    (2006.01)
*A61K 31/505*    (2006.01)

(52) U.S. Cl. .................. 514/419; 548/494; 548/502

(58) Field of Classification Search ............... 548/494, 548/502; 514/419
See application file for complete search history.

(56) References Cited

U.S. PATENT DOCUMENTS

| | | | |
|---|---|---|---|
| 4,739,073 A | 4/1988 | Kathawala | |
| 5,011,930 A | 4/1991 | Fujikawa et al. | |
| 5,354,772 A | 10/1994 | Kathawala | |
| 5,856,336 A | 1/1999 | Fujikawa et al. | |
| 5,872,130 A | 2/1999 | Fujikawa et al. | |
| 6,124,340 A | 9/2000 | Horvath | |
| 6,589,959 B1 | 7/2003 | Taylor | |
| 6,696,479 B2 | 2/2004 | Van Der Schaaf et al. | |

FOREIGN PATENT DOCUMENTS

| | | | |
|---|---|---|---|
| EP | 0521471 B1 | | 10/2000 |
| WO | WO0049014 A1 | | 8/2000 |
| WO | WO 00/71116 | * | 11/2000 |
| WO | WO0160804 A1 | | 8/2001 |
| WO | WO2004014872 A1 | | 2/2004 |

OTHER PUBLICATIONS

Vega et al., PubMed Abstract (Circulation 84(1):118-28) Jul. 1991.*

* cited by examiner

*Primary Examiner*—Deepak Rao

(57) ABSTRACT

The present invention relates to novel anhydrous amorphous forms of bis[(E)[4-(4-fluorophenyl)isopropyl[methyl(methylsulfonyl)amino]pyrimidinyl](3R,5S)-3,5-dihydroxyheptenoic acid]calcium salt (rosuvastatin calcium), (±)7-(3-(4-fluorophenyl)-1-(1-methylethyl)-1H-indol-2-yl)3,5-dihydroxy heptenoic acid monosodium salt (fluvastatin sodium) and bis[(E)-3,5-dihydroxy-7-[4'-(4"-fluorophenyl)-2'-cyclopropyl-quinolin-3'-hept-6-enoic acid]calcium salt (pitavastatin calcium), to processes for their preparation, to pharmaceutical compositions containing them and to methods of treatment using the same. The rosuvastatin calcium, pitavastatin calcium and fluvastatin sodium obtained are known valuable agents useful in treating hyperlipidemia and hypercholestrolemia.

15 Claims, 3 Drawing Sheets

ANHYDROUS AMORPHOUS FORM OF FLUVASTATIN SODIUM

FIELD OF THE INVENTION

The present invention is directed to novel anhydrous amorphous forms of rosuvastatin calcium, pitavastatin calcium and fluvastatin sodium. The invention also relates to processes for preparing their anhydrous amorphous forms, to pharmaceutical compositions containing them, and to methods of treatment using the same.

BACKGROUND OF THE INVENTION

Rosuvastatin calcium, chemically known as bis[(E)[4-(4-fluorophenyl)isopropyl[methyl(methylsulfonyl)amino]pyrimidinyl](3R,5S)-3,5-dihydroxyhept enoic acid]calcium salt, is represented by the Formula I:

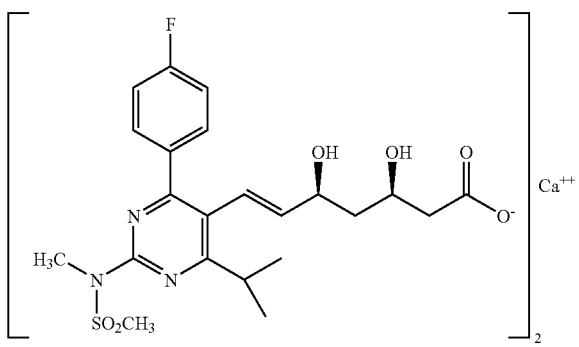

Fluvastatin sodium is known by its chemical name (±)7-(3-(4-fluorophenyl)-1-(1-methylethyl)-1H-indol-2-yl)-3,5-dihydroxy heptenoic acid monosodium salt. Fluvastatin sodium is a racemic mixture of the (3R,5S)- and the (3S,5R)-enantiomer and has the following Formula II:

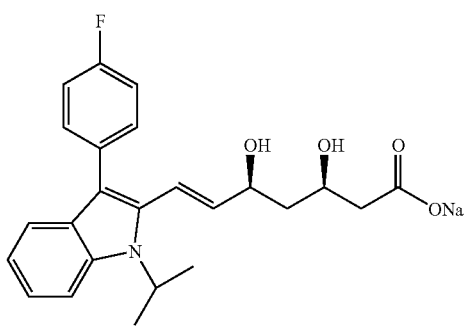

Pitavastatin calcium is the common chemical name for bis[(E)-3,5-dihydroxy-7-[4'-(4''-fluorophenyl)-2'-cyclopropyl-quinolin-3'-hept-6-enoic acid]calcium salt, is represented by the Formula III:

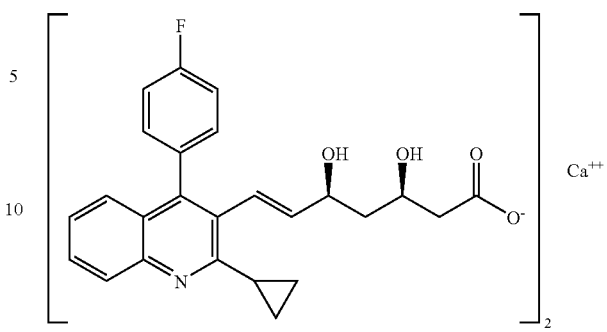

Fluvastatin sodium, pitavastatin calcium and rosuvastatin calcium, hereinafter referred to as "the Agents", are members of the class of drugs called statins. Statin drugs are currently the most therapeutically effective drugs available for reducing low-density lipoprotein (LDL) particle concentration in the blood stream of patients at risk for cardiovascular disease. The Agents are potent inhibitors of the enzyme 3-hydroxy methylglutaryl-coenzyme Areductase (HMG CoA reductase) and are useful as pharmaceutical agents, for example in the treatment of hyperlipidemia, hypercholesterolemia and atherosclerosis, as well as other diseases or conditions in which HMG CoA reductase is implicated.

European Patent Application, Publication No. 521471 (hereinafter EP 0521471 B1), discloses an amorphous (powder) form of rosuvastatin calcium. International Patent Applications WO 00/49014 A1, WO 01/60804 A1 and WO 04/014872 A1 also disclose a non-crystalline form of rosuvastatin calcium. Both powder and non-crystalline rosuvastatin calcium described in these four references are hydrate amorphous forms of rosuvastatin calcium, which is prepared by dissolving the corresponding sodium salt in water, adding calcium chloride in water and collecting the resultant precipitate by filtration. The hydrate amorphous form is usually not very stable and thus often not ideal for the preparation of pharmaceutical composition. U.S. Pat. No. 6,589,959 B1, discloses a hydrate crystalline form (Form A) of rosuvastatin calcium and a method for its preparation.

Pitavastatin, its calcium salt (2:1) and its lactone are disclosed in three related U.S. patents (U.S. Pat. Nos. 5,011,930 A, 5,856,336 A and 5,872,130 A). In the 930' patent, pitavastatin sodium is prepared by converting ethyl (E)-3,5-dihodroxy[4'-(4''-fluorophenyl)-2'-(I cyclopropyl)-quinolin-3'-yl]-hept enoate, to the sodium salt in accordance to Example 2 by using an aqueous solution of sodium hydroxide. The compound is dissolved in ethanol, to which an aqueous solution of sodium hydroxide is added. The resulting mixture is stirred and the ethanol is removed under reduced pressure. Water is then added, and the mixture is further extracted with ether. The aqueous layer is then lyophilized to obtain the final product, or the aqueous layer is weakly acidified with a dilute solution of hydrochloric acid. The acidified aqueous layer is then extracted with ether. After extraction, the ether layer is dried over magnesium sulphate. Then the ether is removed under reduced pressure to obtain the sodium salt. The '930 patent and its related patents do not disclose the procedure for preparing the calcium salt of pitavastatin, and do not disclose amorphous or crystalline forms of pitavastatin calcium as well.

Fluvastatin as well as its sodium salt are disclosed in U.S. Pat. No. 4,739,073. In this patent, fluvastatin sodium is obtained by lyophilization. U.S. Pat. No. 6,124,340 A describes that lyophilization of fluvastatin sodium yields a mixture of a crystalline form (designated as Form A) and amorphous material. This patent further discloses a new crystalline form (designated as Form B) of fluvastatin sodium. The amorphous material obtained in these patents is not pure and contains about 50% crystalline forms. The estimated amount of form A obtained by lyophilization as described in these patents is about 50%. U.S. Pat. No. 6,696,479 B2 discloses additional four crystalline hydrates forms (Form C, D, E and F) of fluvastatin sodium.

The amorphous material of fluvastatin sodium obtained in these patents is also a hydrate, due to the use of a mixture of organic solvent and water as solvents. The hydrate amorphous form is often not very stable and not ideal for the preparation of pharmaceutical composition. An anhydrous amorphous form is often more stable and easier to purify than the corresponding hydrate amorphous form.

It has been disclosed earlier that the amorphous forms in a number of drugs exhibit different dissolution characteristics and in some cases different bioavailability patterns compared to crystalline forms [Konne T., Chem Pharm Bull, 38, 2003 (1990)]. For some therapeutic indications one bioavailability pattern may be favored over another. An amorphous form Cefuroxime axietil is good example for exhibiting higher bioavailability and the crystalline forms. Atorvastatin calcium, which is a member of the statin drugs, has been found that its crystalline forms are less readily soluble than the amorphous form, which may cause problems in the bioavailability of atorvastatin in the body.

Therefore, there is a need to search new forms of rosuvastatin calcium, pitavastatin calcium and fluvastatin sodium.

SUMMARY OF THE INVENTION

We have now surprisingly and unexpectedly discovered that novel anhydrous amorphous forms of rosuvastatin calcium, pitavastatin calcium and fluvastatin sodium, hereinafter referred to as "the Agents", can be prepared.

Accordingly, the present invention aims to provide novel anhydrous amorphous forms of bis[(E)[4-(4-fluorophenyl) isopropyl[methyl(methylsulfonyl)amino]pyrimidin yl](3R,5S)-3,5-dihydroxyhept enoic acid]calcium salts (rosuvastatin calcium), (E)-3,5-dihydroxy-7-[4'-(4"-fluorophenyl)-2'-cyclopropyl-quinolin-3'-hept-6-enoic acid calcium salt (pitavastatin calcium), and (±)7-(3-(4-fluorophenyl)-1-(1-methylethyl)-1H-indol-2-yl)-3,5-dihydroxy heptenoic acid monosodium salt (fluvastatin sodium).

Another embodiment of the present invention is a pharmaceutical composition for administering effective amount novel anhydrous amorphous forms of the Agents in unit dosage form.

According to a further embodiment of the invention is a method of treating hyperlipidemia, hypercholesterolemia and atherosclerosis, as well as other diseases or conditions in which HMG CoA reductase is implicated, with a medicament made by using an effective amount of novel anhydrous amorphous forms of the Agents.

A still another embodiment of the present invention is to provide a process for the preparation of the anhydrous amorphous forms of the Agents. The anhydrous amorphous forms of the Agents are prepared by:
i) dissolving the hydrate amorphous or crystalline materials of the Agents in non-hydroxylic solvent.
ii) adding suitable the non-polar solvent and recovering anhydrous amorphous forms of the Agents from a solution thereof, by solvent precipitation, isolating and drying the product.

A further embodiment of the present invention is to provide a process for the preparation of the anhydrous amorphous forms of the Agents. The anhydrous amorphous forms of the Agents are prepared by:
i) dissolving the crude amorphous or crystalline forms of the Agents in straight or branched chain alcohol containing C1-C4 carbon atoms or a mixture of such alkanols under heating.
ii) isolating the anhydrous amorphous forms of the Agents precipitated after cooling.

BRIEF DESCRIPTION OF THE ACCOMPANYING DRAWINGS

DETAILED DESCRIPTION OF THE INVENTION

Figure 1:
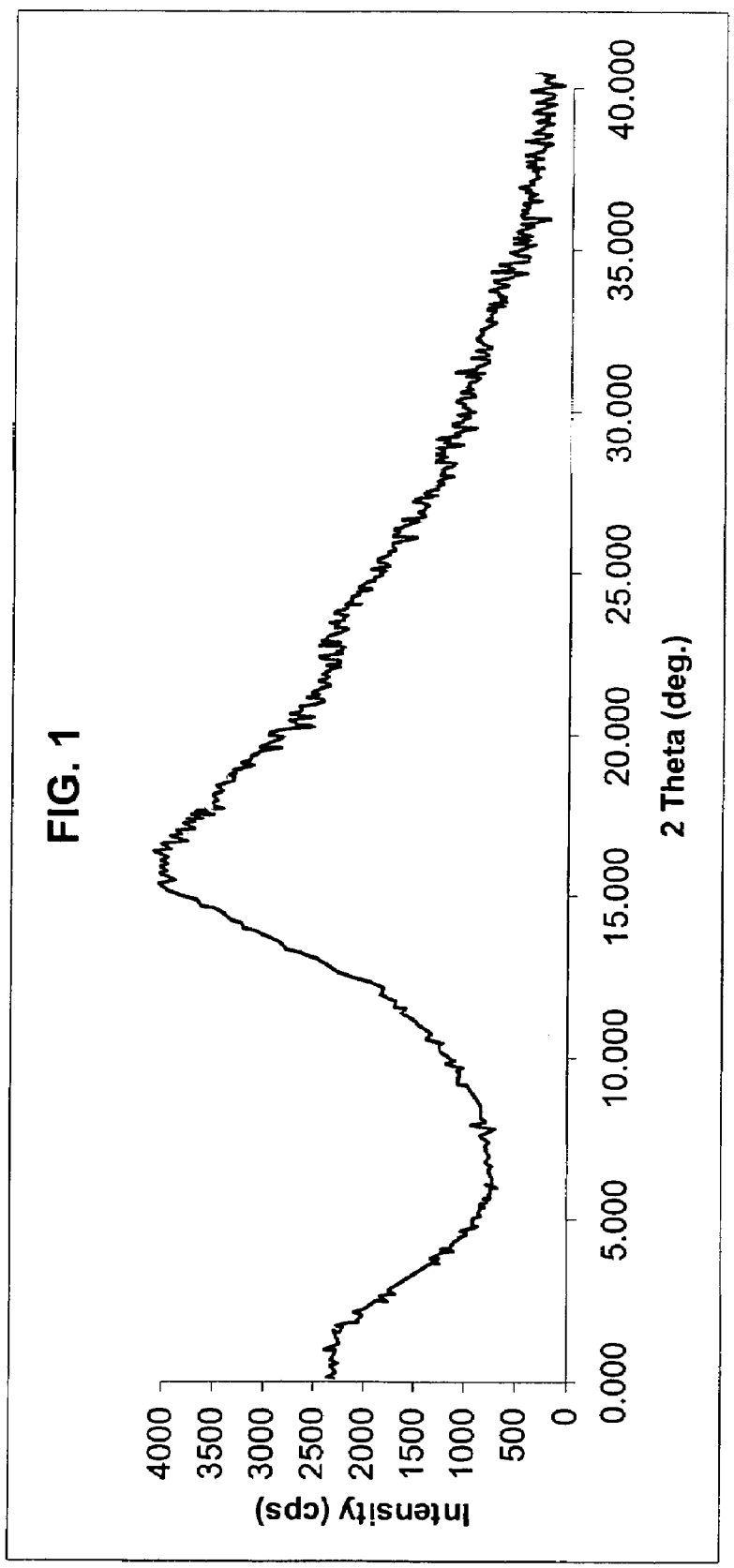
FIG. 1 is X-ray powder diffractogram of novel anhydrous amorphous form of rosuvastatin calcium.

As previously described, rosuvastatin calcium, pitavastatin calcium and fluvastatin sodium are potent inhibitors of the enzyme, HMG-CoA reductase and are useful as hypolipidemic and hypocholesterolemic agents.

The present invention provides novel anhydrous amorphous forms of bis[(E)[4-(4-fluorophenyl)isopropyl[methyl (methylsulfonyl)amino]pyrimidin yl](3R,5S)-3,5-dihydroxyhept enoic acid]calcium salts (rosuvastatin calcium), (E)-3,5-dihydrox-7-[4'-(4"-fluorophenyl)-2'-cyclopropyl-quinolin-3'-hept-6-enoic acid calcium salt (pitavastatin calcium), and (±)7-(3-(4-fluorophenyl)-1-(1-methylethyl)-1H-indol-2-yl)-3,5-dihydroxy heptenoic acid monosodium salt (fluvastatin sodium).

The present invention further provides novel anhydrous amorphous form of bis[(E)[4-(4-fluorophenyl)isopropyl [methyl(methylsulfonyl)amino]pyrimidin yl](3R,5S)-3,5-dihydroxyhept enoic acid]calcium salts (rosuvastatin calcium).

The present invention still provides novel anhydrous amorphous form of bis[(E)-3,5-dihydrox-7-[4'-(4"-fluorophenyl)-2'-cyclopropyl-quinolin-3'-hept-6-enoic acid]calcium salt (pitavastatin calcium).

The present invention again provides novel anhydrous amorphous form of (±)7-(3-(4-fluorophenyl)-1-(1-methylethyl)-1H-indol-2-yl)-3,5-dihydroxy heptenoic acid monosodium salt (fluvastatin sodium).

The present invention also provides a process for preparation of novel anhydrous amorphous forms of rosuvastatin calcium, pitavastatin calcium and fluvastatin sodium, hereinafter referred to as "the Agents".

The present invention further provides a process of preparing a novel anhydrous amorphous form of bis[(E)[4-(4-fluorophenyl)isopropyl[methyl(methylsulfonyl)amino]pyrimidin yl](3R,5S)-3,5-dihydroxyhept enoic acid]calcium salts (rosuvastatin calcium).

The present invention still provides a process of preparing a novel anhydrous amorphous form of bis[(E)-3,5dihydrox-7-[4'-(4"-fluorophenyl)-2'-cyclopropyl-quinolin-3'-hept-6-enoic acid]calcium salt (pitavastatin calcium).

The present invention again provides a process of preparing a novel anhydrous amorphous form of (±)7-(3-(4-fluorophenyl)-1-(1-methylethyl)-1H-indol-2-yl)-3,5-dihydroxy heptenoic acid monosodium salt (fluvastatin sodium).

The process for preparing amorphous forms of the Agents comprises:
  (a) dissolving crude or pure hydrate amorphous rosuvastatin calcium (as described EP patent No. 0521471 B1) or crystalline rosuvastatin calcium hydrate (e.g., form A, as described in U.S. Pat. No. 6,589,959 B1) or crude pitavastatin calcium (as described in Example 4 of this invention) or a mixture of amorphous and crystalline (Form A) of fluvastatin sodium (as described in U.S. Pat. Nos. 4,739,073 and 6,124,340 A) in a non-hydroxylic solvent under heating;
  (b) adding a non-polar anti-solvent to precipitate out the material;
  and (c) removing the solvent by filtration to afford anhydrous amorphous forms of the Agents.

The preparation of crude or pure hydrate amorphous rosuvastatin calcium is described in EP Pat. No. 0521471. The preparation of crystalline rosuvastatin calcium hydrate (form A) is described in U.S. Pat. No. 6,589,959 B1.

The preparation of crude fluvastatin sodium is described in U.S. Pat. No. 4,739,073. U.S. Pat. No. 6,124,340 A teaches the preparation of a mixture of amorphous and crystalline form of fluvastatin sodium. The preparation of hydrate crystalline fluvastatin sodium (form C, D, E, and F) is described in U.S. Pat. No. 6,696,479 B2.

The preparation of pitavastation sodium is described in three related U.S. patents (U.S. Pat. Nos. 5,011,930 A, 5,856,336 A and 5,872,130 A). The preparation of pitavastatin calcium is described in the Example 6 of the present invention. That is, the pitavastatin sodium is converted to pitavastatin calcium by dissolving the corresponding sodium salt in water and ethanol, adding calcium acetate in water and collecting the resultant precipitate by filtration.

The non-hydroxylic solvent of the present invention is selected from a group of solvents, which have the ability to dissolve crude or pure hydrate amorphous or crystalline forms or their mixtures of the Agents, and includes tetrahydrofuran, acetonitrile or their mixtures. Suitable non-polar solvents are selected from a group consisting of: n-hexane, cyclohexane, hexane fraction, heptane fraction or the like. In a preferred embodiment of this invention, the non-hydroxylic solvent is tetrahydrofuran and antisolvent is n-hexane or cyclohexane.

Generally, hydrate amorphous or crystalline forms or their mixtures of the Agents are dissolved in a non-hydroxylic solvent, e.g. tetrahydrofuran, at a concentration of about 2% w/v to about 35% w/v, preferably at a concentration of about 3% w/v to about 15% w/v at ambient temperature to 55° C., preferably at 40° C. to 50° C. A non-polar solvent, preferably n-hexane, cyclohexane or n-heptane, is added at 0° C. to 50° C., preferably at 20° C. to 25° C. The product is recovered by filtration at ambient temperature. Filtration is carried out using nutsche filtration or centrifuge filtration. Filtered material is further dried to remove solvents in a vacuum tray drier, fluid bed drier or a rotary vacuum drier to afford amorphous material. Preferably, material is dried in a vacuum tray drier at about 20° C. to about 75° C. for 6 hours to 20 hours. Most preferably, drying is carried out at about 45° C. to about 60° C. for 15 hours.

Quantity of antisolvent varies from 5 times to 50 times input of hydrate amorphous rosuvastatin calcium or crystalline rosuvastatin calcium (e.g., form A) depending upon its solution in non-hydroxylic solvent. Preferably, the quantity of antisolvent used is about 20 times to about 40 times input of hydrate amorphous or crystalline forms or their mixtures of the Agents to make overall concentration of about 5% w/v to about 2.5% w/v.

It has been unexpectedly found that uniformly anhydrous amorphous forms of rosuvastatin calcium, fluvastatin sodium and pitavastatin calcium can be obtained in a simple and reproducible process as described above.

The present invention further provides a process for preparation of novel anhydrous amorphous forms of rosuvastatin calcium, pitavastatin calcium and fluvastatin sodium, hereinafter referred to as "the Agents".

The present invention provides a process of preparing a novel anhydrous amorphous form of bis[(E)[4-(4-fluorophenyl)isopropyl methyl(methylsulfonyl)amino]pyrimidin yl] (3R,5S)-3,5-dihydroxyhept enoic acid]calcium salts (rosuvastatin calcium).

The present invention still provides a process of preparing a novel anhydrous amorphous form of bis[(E)-3,5-dihydrox-7-[4'-(4"-fluorophenyl)-2'-cyclopropyl-quinolin-3'-hept-6-enoic acid]calcium salt (pitavastatin calcium).

The present invention again provides a process of preparing a novel anhydrous amorphous form of (±)7-(3-(4-fluorophenyl)-1-(1-methylethyl)-1H-indol-2-yl)-3,5-dihydroxy heptenoic acid monosodium salt (fluvastatin sodium).

The process of preparing anhydrous amorphous forms of the Agents comprises:
  (a) dissolving hydrate amorphous or crystalline forms or their mixtures of the Agents in acetonitrile or a straight or branched alkanol containing 1-4 carbon atoms or a mixture of two or more such alkanols under heating.
  (b) cooling the solution to precipitate out the material;
  (c) filtering and drying the precipitate to afford anhydrous amorphous forms of the Agents.

Generally, hydrate amorphous or crystalline forms or their mixtures of the Agents are dissolved in acetonitrile or an alkanol solvent, e.g., ethanol, at a concentration of about 1% w/v to about 35% w/v, preferably at a concentration of about 2% w/v to about 15% w/v at ambient temperature to 55° C., preferably at 40° C. to 50° C. The hot solution is then cooled to 0° C. to 25° C., preferably at 5° C. to 25° C. The product is recovered by filtration at ambient temperature. Filtration is carried out using nutsche filtration or centrifuge filtration. Filtered material is further dried to remove solvents in a vacuum tray drier, fluid bed drier or a rotary vacuum drier to afford amorphous material. Preferably, material is dried in a vacuum tray drier at about 20° C. to about 75° C. for 6 hours to 20 hours. Most preferably, drying is carried out at about 45° C to about 60° C. for 15 hours.

It has been unexpectedly found that uniformly anhydrous amorphous forms of rosuvastatin calcium, fluvastatin sodium and pitavastatin calcium can be obtained in a simple and reproducible manner as described above.

According to the process of the present invention, methanol, ethanol, n-propanol, isopropanol or branched-chain butanols can be used as alkanol containing 1-4 carbon atoms. It is preferred to use isopropanol or ethanol, or a mixture of isopropanol and ethanol. The process may also be carried out by using a mixture of two or more alkanols.

According to the process of the present invention, acetonitrile can also be used. The process may also be carried out by using a mixture of acetonitrile and one or more alkanols.

For starting material, one may preferably use crude or pure hydrate amorphous rosuvastatin calcium (as described in EP Pat. No. 0521471 B1) or crystalline rosuvastatin calcium (e.g., form A, as described in U.S. Pat. No. 6,589,959 B1). One may also use crude or pure hydrate amorphous or crystalline or their mixtures of pitavastatin calcium that can be obtained by Example 4 of this invention as the starting material. In addition, one may also use crude or pure hydrate amorphous or crystalline or their mixtures of fluvatsatin sodium that can be obtained by following the procedure described in patents (U.S. Pat. Nos. 4,739,073 and 6,124,340 A) as the starting material.

According to a preferred form of realization of the process of the present invention one may proceed as follows:

The starting material is dissolved in an alkanol containing 1-4 carbon atoms under heating, advantageously at the boiling point of the solvent. One may proceed preferably by filtering the solution, allowing the filtrate to cool to room temperature and allowing the suspension to stand in the cold. The precipitated anhydrous amorphous forms of the Agents is isolated by filtration or centrifuging, washed with the cold alkanol containing 1-4 carbon atoms used for dissolving starting material, and finally dried in vacuum. One may also work by filtering the hot solution into boiling 1-4 carbon alkanol and then proceeding as described above.

Further details of the present invention are to be found in the Examples without limiting the scope of protection to said Examples.

Figure 2:
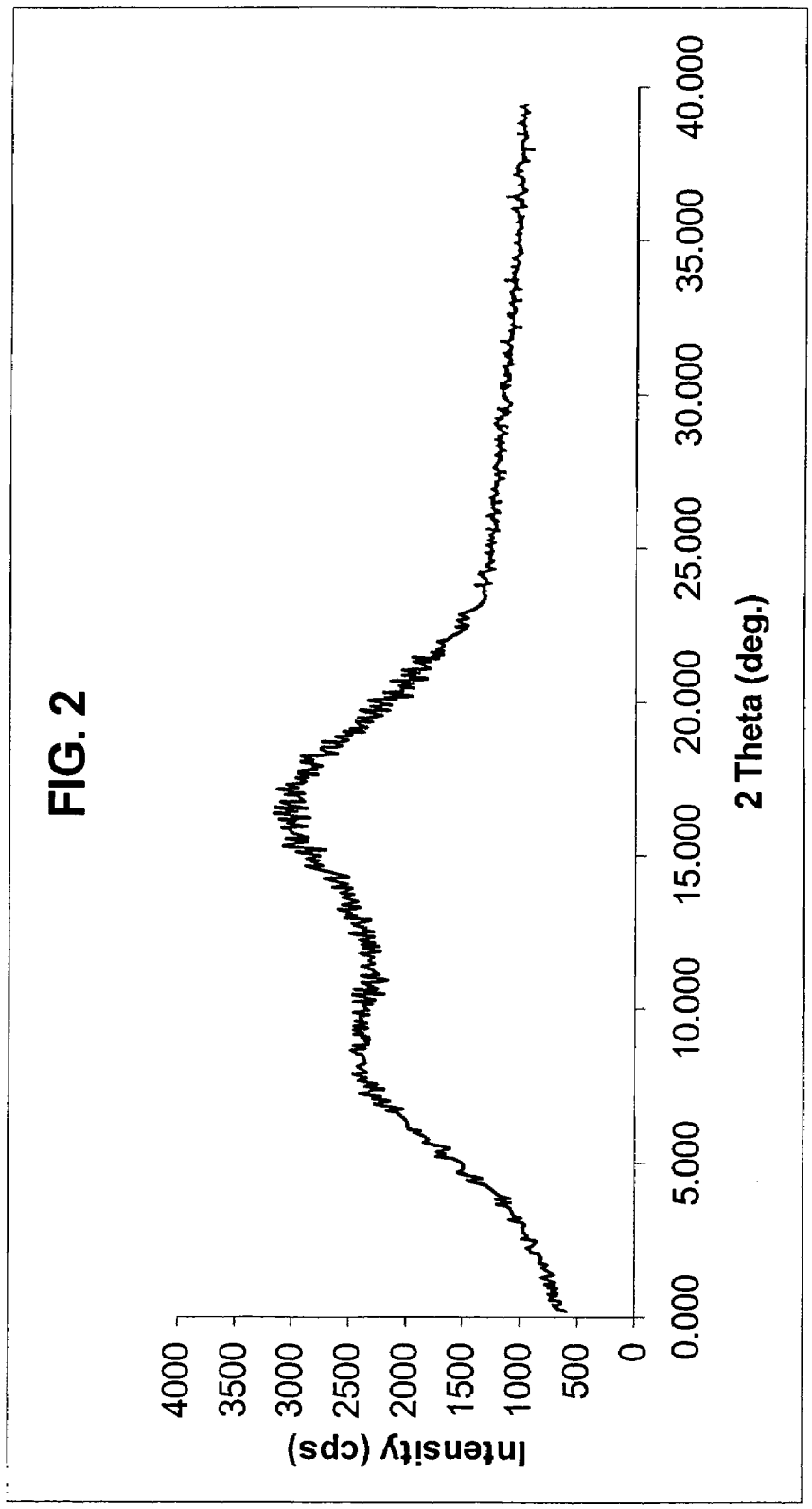
FIG. 2 is X-ray powder diffractogram of novel anhydrous amorphous form of pitavastatin calcium.
Figure 3:
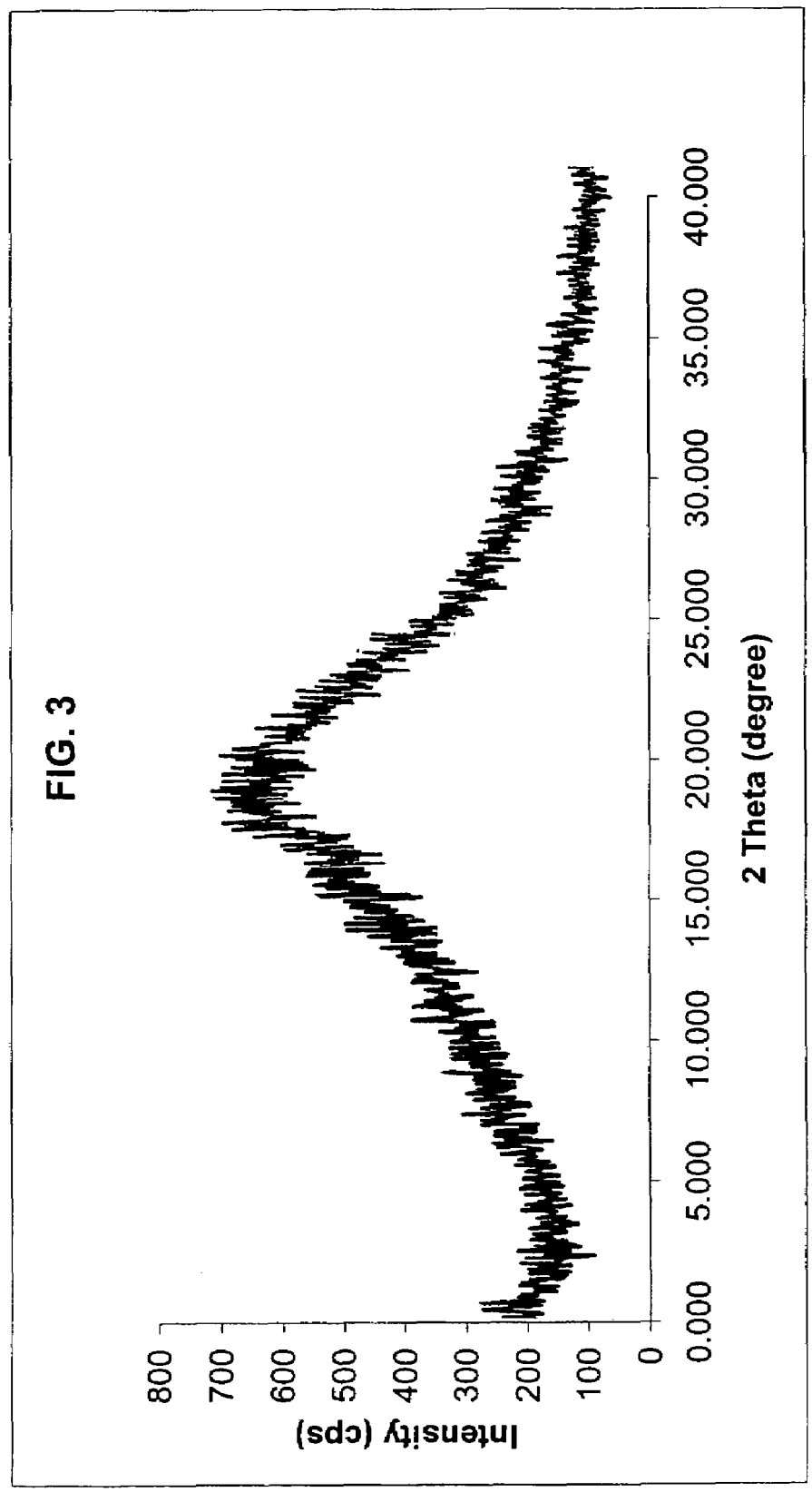
FIG. 3 is X-ray powder diffractogram of novel anhydrous amorphous form of fluvastatin sodium.

Anhydrous amorphous forms of the Agents prepared according to the process of the present invention may be characterized by its x-ray powder diffration pattern, as shown in the accompanied drawings of FIG. 1, FIG. 2 and FIG. 3. X-ray powder diffraction patterns (FIG. 1, FIG. 2 and FIG. 3) show no peaks which are characteristic of anhydrous amorphous forms of rosuvastatin calcium, pitavastatin calcium and fluvastatin sodium, thus demonstrating the amorphous nature of the product.

Another embodiment of the present invention is a pharmaceutical composition for administering effective amount of novel anhydrous amorphous forms of rosuvastatin calcium, pitavastatin calcium and fluvastatin sodium, hereinafter referred to as "the Agents", in unit dosage forms.

The unit dosage forms can be administered in a wide variety of oral and parenteral dosage forms. Thus, the compound of the present invention can be administered by injection, that is, intravenously, intramuscularly, intracutaneously, subcutaneously, intraduodenally, or intraperitoneally. Also, the anhydrous amorphous forms of the Agents of the present invention can be administered by inhalation, for example, intranasally. Additionally, the compound of the present invention can be administered transdermally. It will be obvious to those skilled in the art that the following dosage forms may comprise as the active component, either anhydrous amorphous forms of the Agents, or a corresponding pharmaceutically acceptable salt of a compound of the present invention.

For preparing pharmaceutical compositions from anhydrous amorphous forms of the Agents of the present invention, pharmaceutically acceptable carriers can be either solid or liquid.

Solid form compositions include powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired.

The powders and tablets preferably contain from one or ten to about seventy percent of the active compound. Suitable carriers are magnesium carbonate, magnesium stearate, talc, sugar or lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component—25 in water with viscous material, such as natural or synthetic gums, resins, methylcellulose, sodium carboxymethylcellulose, and other well-known suspending agents.

Also included are solid form compositions that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical composition is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.5 mg to 100 mg, preferably 1 mg to 50 mg according to the particular application and the potency of the active component. The composition can, if desired, also contain other compatible therapeutic agents.

According to a further embodiment of the invention is a method of treating a disease condition wherein inhibition of HMG CoA reductase beneficial, which comprises administering to warm-blooded mammal, particularly a human, and effective amount of an anhydrous amorphous form of rosuvastatin calcium, pitavastatin calcium or fluvastatin sodium. As inhibitors of HMG-CoA, novel anhydrous amorphous forms of rosuvastatin calcium, pitavastatin calcium and fluvastatin sodium are useful hypolipidemic and hypocholesterolemic compounds, and thus are useful in the treatment of hyperlipidemia, hypercholesterolemia and atherosclerosis, as well as other diseases or conditions in which HMG CoA reductase is implicated.

In therapeutic use as hypolipidemic and/or hypocholesterolemic compounds, the anhydrous amorphous forms of rosuvastatin calcium, pitavastatin calcium and fluvastatin sodium utilized in the pharmaceutical method of this invention is administered at the initial dosage of about 0.5 mg to about 50 mg daily. A daily dose range of about 1 mg to about 40 mg is preferred. The dosages, however, may be varied depending upon the requirements of the patient, the severity of the condition being treated/ and the compound being employed. Determination of the proper dosage for a particular situation is within the skill of the art. Generally, treatment is initiated with smaller dosages, which are less than the optimum dose of the compound. Thereafter, the dosage is increased by small increments until the optimum effect under the circumstance is reached. For convenience, the total daily dosage may be divided and administered in portions during the day if desired.

While the present invention has been described in terms of its specific embodiments, certain modifications and equivalents will be apparent to those skilled in the art and are intended to be included within the scope of the present invention.

The following examples are provided to illustrate specific embodiments of the present invention. They are not intended to be limiting in any way.

EXAMPLES

Example 1

Preparation of anhydrous amorphous form of bis[(E)[4-(4-fluorophenyl)isopropyl methyl(methylsulfonyl)amino] pyrimidin yl](3R,5S)-3,5-dihydroxyhept enoic acid]calcium salts (rosuvastatin calcium)

Method A Crude rosuvastatin calcium powder (2 g, prepared according to Example 2 of EP patent No. 0521471 B1) was dissolved in tetrahydrofuran (40 ml) under stirring at 40° C. Clear solution so obtained was added slowly to cyclohexane (80 ml) under nitrogen atmosphere it was vigorously stirred maintaining temperature at 20-25° C. The precipitated product was centrifuged and dried under vacuum at about 60° C. for 15 hours. Rosuvastatin calcium (1.6 g, yield 80%) in anhydrous amorphous form was obtained having residual solvent levels of 0.01% w/w tetrahydrofuran and 0.4% w/w cyclohexane. X-ray powder diffraction pattern (FIG. 1 as shown in the accompanied drawings) demonstrate the amorphous nature of the product.

Method B Crystalline rosuvastatin calcium hydrate (1 g, form A, prepared according to Example 1 of U.S. Pat. No. 6,589,959 B1) was dissolved in tetrahydrofuran (20 ml) under stirring at 40° C. Clear solution so obtained was added slowly to cyclohexane (40 ml) under nitrogen atmosphere. It was vigorously stirred maintaining temperature at 20-25° C. The precipitated product was centrifuged and dried under vacuum at about 60° C. for 15 hours. Rosuvastatin calcium (0.72 g, yield 72%) in anhydrous amorphous form was obtained having residual solvent levels of 0.01% w/w tetrahydroftran and 0.5% w/w cyclohexane. X-ray powder diffraction pattern (FIG. 1 as shown in the accompanied drawings) demonstrate the amorphous nature of the product.

Example 2

Preparation of anhydrous amorphous form of bis[(E)[4-(4-fluorophenyl)isopropyl methyl(methylsulfonyl)amino] pyrimidin yl](3R,5S)-3,5-dihydroxyhept enoic acid]calcium salts (rosuvastatin calcium)

1.0 g of crude hydrate amorphous rosuvastatin calcium salt prepared according to Example 2 of EP patent No. 0521471 B1 is heated to boiling in 50 ml of ethanol until the material goes into solution. The hot solution obtained is filtered into 50 ml of boiling 2-propanol and allowed to cool to room temperature, while the precipitation of the anhydrous amorphous rosuvastatin calcium salt begins. The suspension obtained is allowed to stand at 40° C. for 4 hours, and then filtered, washed with cold ethanol (4° C.) and dried in vacuum at room temperature. Thus 0.74 g of anhydrous amorphous rosuvastatin calcium salt is obtained (yield 74%). X-ray powder diffraction examination (FIG. 1 as shown in the accompanied drawings) confirmed the amorphous nature of the product.

Example 3

Preparation of anhydrous amorphous form of bis[(E)[4-(4-fluorophenyl)isopropyl methyl(methylsulfonyl)amino] pyrimidin yl](3R,5S)-3,5-dihydroxyhept enoic acid]calcium salts (rosuvastatin calcium)

Method A 1.0 g of crude rosuvastatin calcium powder (prepared according to Example 2 of EP patent No. 0521471 B1) in 80 ml of 2-propanol is heated to boiling until the material goes into solution. The hot solution thus obtained is filtered into 20 ml of boiling 2-propanol and allowed to cool to 10° C. The 2-propanol suspension is allowed to stand at 40° C. for 4 hours. The precipitated anhydrous amorphous product is filtered off, washed with cold 2-propanol (4° C.) and dried in vacuum at room temperature. 0.78 g of uniformly anhydrous amorphous rosuvastatin calcium is obtained (yield 78%). X-ray powder diffraction examination confirmed the amorphous nature of the product.

Method B 1.0 g of crude rosuvastatin calcium powder prepared according to Example 2 of EP patent No. 0521471 B1 is heated to 40° C. in 50 ml of acetonitrile until the material goes into solution. The hot solution thus obtained is filtered into 20 ml of acetonitrile and allowed to cool to room temperature. The acetonitrile suspension is allowed to stand at 40° C. for 4 hours. The precipitated anhydrous amorphous product is filtered off, washed with cold acetonitrile (4° C.) and dried in vacuum at room temperature. 0.82 (yield 82%) g of uniformly anhydrous amorphous rosuvastatin calcium is obtained. X-ray powder diffraction examination (FIG. 1 as shown in the accompanied drawings) confirmed the amorphous nature of the product.

Example 4

Preparation of anhydrous amorphous form of (±)7-(3-(4-fluorophenyl)-1-(1-methylethyl)-1H-indol-2-yl)-3,5-dihydroxy heptenoic acid monosodium salt (fluvastatin sodium)

Fluvastatin sodium (2 g, prepared according to Example 8 of U.S. Pat. No. 4,739,073 and Example 14D of U.S. Pat. No. 5,354,772 A) was dissolved in tetrahydrofuran (20 ml) under stirring at 40° C. Clear solution so obtained was added slowly to cyclohexane (70 ml) under nitrogen atmosphere. It was vigorously stirred maintaining temperature at 20-25° C. The precipitated product was centrifuged and dried under vacuum at about 50° C. for 15 hours. Fluvastatin sodium (1.6 g, yield 80%) in anhydrous amorphous form was obtained having residual solvent levels of 0.01% w/w tetrahydrofuran and 0.3% w/w cyclohexane. X-ray powder diffraction pattern (FIG. 3 as shown in the accompanied drawings) demonstrate the amorphous nature of the product.

Example 5

Preparation of anhydrous amorphous form of (±)7-(3-(4-fluorophenyl)-1-(1-methylethyl)-1H-indol-2-yl)-3,5-dihydroxy heptenoic acid monosodium salt (fluvastatin sodium)

2 g of fluvastatin sodium (prepared according to Example 8 of U.S. Pat. No. 4,739,073 and Example 14D of U.S. Pat. No. 5,354,772 A) heated to boiling in 35 ml of ethanol until the material goes into solution. The hot solution obtained is filtered into 80 ml of boiling 2-propanol and allowed to cool to room temperature, while the precipitation of the anhydrous amorphous form of fluvastatin sodium salt begins. The suspension obtained is allowed to stand at 40° C. for 4 hours, and then filtered, washed with cold ethanol (4° C.) and dried in vacuum at room temperature. Thus 1.4 g of anhydrous amorphous fluvastatin sodium salt is obtained (yield 70%). X-ray powder diffraction examination (FIG. 3 as shown in the accompanied drawings) confirmed the amorphous nature of the product.

Example 6

Preparation of bis[(E)-3,5-dihydroxy-7-[4'-(4"-fluorophenyl)-2'-cyclopropyl-quinolin-3'-hept-6-enoic acid]calcium salt (pitavastatin calcium)

Pitavastatin sodium (5.22 g) prepared according to U.S. Pat. Nos. 5,011,930 A, 5,856,336 A and 5,872,130 A is dissolved in a mixture of 75 ml of water and 15 ml of ethanol and stirred at room temperature under a nitrogen atmosphere. Successively 12 ml of 1 mol/L calcium acetate in water is added drop wise thereto over 20 minutes. The reaction mixture is stirred at the ambient temperature for 3 hours, and the resulting precipitate is collected, washed with water and dried to give 4.5 g of crude pitavastatin calcium salt material.

Example 7

Preparation of anhydrous amorphous form of bis[(E)-3,5-dihydroxy-7-[4'-(4"-fluorophenyl)-2'-cyclopropyl-quinolin-3'-hept-6-enoic acid]calcium salt (pitavastatin calcium)

Pitavastatin sodium (1 g, prepared according to Example 6 of this invention) was dissolved in tetrahydrofuran (10 ml) under stirring at 40° C. Clear solution so obtained was added slowly to cyclohexane (35 ml) under nitrogen atmosphere. It was vigorously stirred maintaining temperature at 20-25° C. The precipitated product was centrifuged and dried under vacuum at about 50° C. for 15 hours. Pitavastatin calcium (0.8 g, yield 80%) in anhydrous amorphous form was obtained having residual solvent levels of 0.01% w/w tetrahydrofuran and 0.4% w/w cyclohexane. X-ray powder diffraction pattern (FIG. 2 as shown in the accompanied drawings) demonstrate the amorphous nature of the product.

Example 8

Preparation of anhydrous amorphous form of bis[(E)-3,5-dihydroxy-7-[4'-(4"-fluorophenyl)-2'-cyclopropyl-quinolin-3'-hept-6-enoic acid]calcium salt (pitavastatin calcium)

Pitavastatin sodium (1 g, prepared according to Example 6 of this invention) heated to boiling in 20 ml of ethanol until the material goes into solution. The hot solution obtained is filtered into 20 ml of boiling 2-propanol and allowed to cool to room temperature, while the precipitation of the anhydrous amorphous form of pitavastatin calcium salt begins. The suspension obtained is allowed to stand at 40° C. for 4 hours, and then filtered, washed with cold ethanol (4° C.) and dried in vacuum at room temperature. Thus 0.71 g of anhydrous amorphous form of pitavastatin calcium salt is obtained (yield 71%). X-ray powder diffraction examination (FIG. 2 as shown in the accompanied drawings) confirmed the amorphous nature of the product.

The X-ray powder diffraction pattern of the products are shown in FIG. 1, FIG. 2 and FIG. 3, respectively. Owing to their disordered structure, amorphous materials do not display sharp peaks on the diffraction pattern; they are characterized only by flattened curves. With the use of X-ray diffraction one can therefore unambiguously verify the amorphous state of the products prepared in this invention.

I claim:

1. Anhydrous amorphous fluvastatin sodium, wherein its X-ray powder diffraction pattern is substantially in accordance with FIG. 3.

2. A process for preparation of anhydrous amorphous fluvastatin sodium of claim 1, comprising steps of:
    (a) Dissolving crude or pure hydrate amorphous or crystalline form or their mixtures of fluvastatin sodium in a non-hydroxylic solvent;
    (b) Adding a non-polar hydrocarbon anti-solvent or adding the dissolved fluvastatin sodium to the non-polar anti-solvent to precipitate out product;
    and (c) removing the solvent by filtration to afford anhydrous amorphous fluvastatin sodium.

3. The process according to claim 2, wherein the non-hydroxylic solvent is tetrahydrofuran and anti-solvent is chosen from a group of non-polar hydrocarbon solvents comprising n-hexane, cyclohexane or n-heptane.

4. The process according to claim 2, wherein the non-hydroxylic solvent is tetrahydrofuran and anti-solvent is n-hexane.

5. The process according to claim 2, wherein the non-hydroxylic solvent is tetrahydrofuran and anti-solvent is cylcohexane.

6. The process according to claim 2, wherein the non-hydroxylic solvent is tetrahydrofuran and anti-solvent is n-heptane.

7. The process according to any of claims 2, and 3-6, which comprises cooling the solution and isolating the precipitated anhydrous amorphous form by filtration or centrifuging.

8. A process for the preparation of anhydrous amorphous fluvastatin sodium of claim 1 by dissolving crude or pure hydrate amorphous or crystalline forms or their mixtures of fluvastatin sodium in acetonitrile or in straight or branched alkanol containing 1-4 carbon atoms or a mixture of such alkanols under heating and isolating the anhydrous amorphous fluvastatin sodium precipitated after cooling.

9. The process according to claim 8, wherein the alkanol solvent is selected from methanol, ethanol, isopropanol, butanol or their mixtures.

10. The process according to claim 8, wherein the alkanol solvent is selected from ethanol and isopropanol.

11. The process according to claim 8, which comprises using acetonitrile or a mixture of acetonitrile and one or more alkanols.

12. The process according to claim 8, which comprises dissolving fluvastatin sodium in alkanols or acetonitrile at the boiling point of the solvent.

13. The process according to any of claims 8 and 9-12, which comprises cooling the solution and isolating the precipitated anhydrous amorphous fluvastatin sodium by filtration or centrifuging.

14. A pharmaceutical composition comprising an anhydrous amorphous fluvatsatin sodium of claim 1 and pharmaceutically acceptable carrier, diluent, excipient, additive, filler, lubricant, solvent binder or stabilizer.

15. A pharmaceutical composition according to claim 14, in the form of a tablet, troche, powder, syrup, patch, liposome, injection, dispersion, suspension, solutions, capsule, cream, ointment or aerosol.

* * * * *